United States Patent [19]

Cartmell

[11] Patent Number: 4,800,878

[45] Date of Patent: Jan. 31, 1989

[54] ELECTROSURGICAL KNIFE WITH VISUAL ALARM

[75] Inventor: Robert L. Cartmell, Bellbrook, Ohio

[73] Assignee: Becton, Dickinson and Company, Franklin Lakes, N.J.

[21] Appl. No.: 90,199

[22] Filed: Aug. 26, 1987

[51] Int. Cl.⁴ .............................................. A61B 17/39
[52] U.S. Cl. ................................. 128/303.14; 128/908
[58] Field of Search ....................... 128/303.13, 303.14, 128/303.17, 303.18, 303.19, 741, 908; 219/230

[56] References Cited

U.S. PATENT DOCUMENTS

| | | | |
|---|---|---|---|
| 2,417,530 | 3/1947 | Weiser | 128/303.13 |
| 3,295,414 | 1/1967 | Hein et al. | 128/303.14 X |
| 3,707,149 | 12/1972 | Hao et al. | 128/303.14 |
| 3,807,404 | 4/1974 | Weissman et al. | 128/303.14 |
| 3,870,047 | 3/1975 | Gonser | 128/303.14 |
| 3,875,945 | 4/1975 | Friedman | 128/303.17 X |
| 4,542,741 | 9/1985 | Burgin | 128/303.1 |

FOREIGN PATENT DOCUMENTS 791965  3/1958  United Kingdom ............... 128/741

*Primary Examiner*—Lee S. Cohen
*Attorney, Agent, or Firm*—Robert P. Grindle

[57] ABSTRACT

A disposable electrosurgical knife handle and blade is provided with a built-in warning light positioned on the top of the handle in the surgeon's line of vision during surgical procedures in order to warn, instantly, of unwanted surges in the electrical system which could bring about tissue damage. Because of the arrangement, the surgeon may remove immediately the blade or other cutting instrument fitted into the handle from the surgical site.

6 Claims, 2 Drawing Sheets

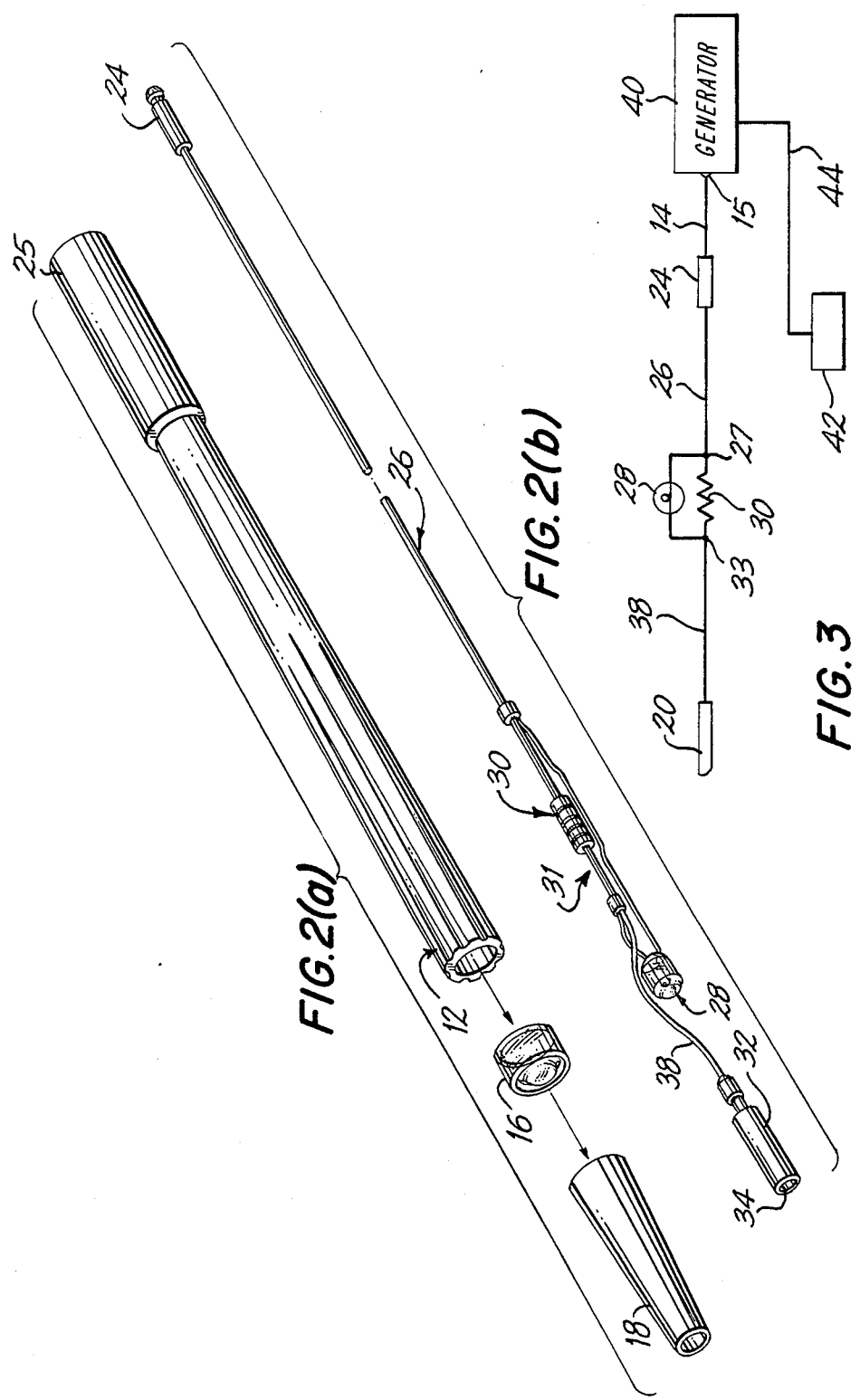

ELECTROSURGICAL KNIFE WITH VISUAL ALARM

BACKGROUND STATEMENT OF THE INVENTION

This invention relates to electrosurgical instruments, and more particularly to an alarm system for such instruments which provides for instant alerting of the surgeon of the presence of a dangerous situation in the electrical system of the device being used. More particularly, this invention relates to a disposable electrosurgical instrument having incorporated into the surface thereof a warning light which is incorporated into the circuitry leading to the electrode forming the blade or other cutting active portion of the instrument.

The arrangement is such that the light is in the direct vision of the surgeon during his surgical procedures so that any variation in the circuitry, such as an unwanted surge of electrical current, is immediately made apparent to the surgeon by the sudden brilliant lighting of the warning lamp of the invention.

In electrosurgery, an electrical current flows through a circuit that begins at a high-frequency oscillator within an electrosurgical unit, goes through an active cable to an active electrode forming the blade of the unit to the patient, and then returns from the patient by way of a dispersive electrode and a cable to the electrosurgical unit. The dispersive electrode has a relatively large contact area to prevent burns to the patient's body.

By contrast, the relatively small contact area between the tissue and the active electrode tip causes a concentration of current (high current density) that heats the tissue at this point, thus allowing for the "electrosurgical" cutting of tissue. However, because of the concentration of current at the cutting point, it is important to have an immediate response when that concentration increases beyond a desired level because of some failure in the electric circuit.

With this invention, provision is made for continuous monitoring of the surgical procedure with the indicator being held in the surgeon's hand so that immediate action may be taken if sudden change occurs in the electronic circuit. This is done without the surgeon having to observe a surgical generator panel, without having to listen for an audio alarm of some kind from the panel or without having to wait for a nurse's observation of the generator's output to correct improper settings.

Thus, with the invention herein, the blade, or other cutting instrument, is the output electrode and it is connected to a surgical generator which is the input source of the device. The active return of the generator is connected to the patient during the electrosurgical procedure. During this procedure, in accordance with the invention herein, a parallel lamp mounted directly upon the disposable handle of the electrical surgical knife unit and a resistor therefor in combination become a passive component for the high frequency current of the generator. Because of this, all current passes through the lamp and the resistor network during operation procedures. Thus, any variation in the current output is immediately disclosed in the lamp, and immediately alerts the surgeon directly in his line of vision so that the blade is immediately removed from the surgical site.

In considering generally the conditions for operation of the invention herein, it should be noted that in operation the lamp's filament resistance is non-linear, and changes from a very low resistance when cold to a relatively high resistance when hot. Thus, in accordance with this invention, a lamp is selected with a sharp change in resistance as current is increased so that the light "turn-on" point is at a chosen current level. Moreover, a proper choice of parallel resistor to operate in combination with the lamp is selected. Typically, the light output is measured at 0.2 amps increments of current. With this arrangement, at 0.4 amps, light output is nearly non-measurable. By contrast, at 0.8 amps, a brilliant source of light is obtained.

Other objects and advantages of this invention will be apparent from the following description, the accompanying drawings, and the appended claims.

DESCRIPTION OF THE DRAWINGS

FIG. 2(a) is an exploded view of the device of FIG. 1;

FIG. 2(b) is an exploded view of the internal components of the device of FIGS. 1 and 2a showing the arrangement of the internal components thereof; and FIG. 3 is a schematic illustration of a circuit diagram of the electrosurgical knife of the invention.

BRIEF DESCRIPTION OF THE DRAWINGS

Figure 1:
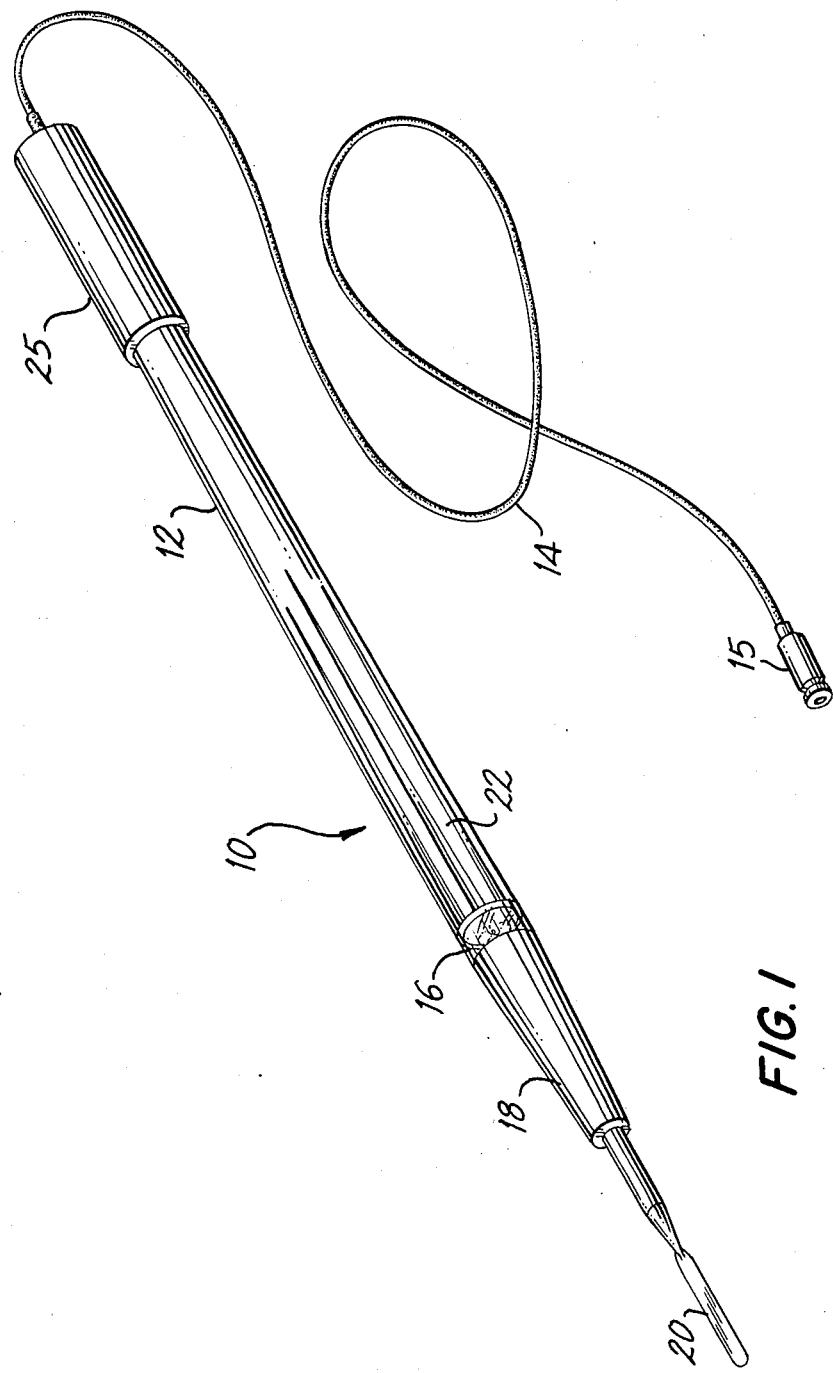
FIG. 1 is a perspective view of an electrosurgical knife and illustrating the invention.

Before describing this invention in more detail, it may be well to note that in a preferred embodiment of the invention, a surgical instrument is provided which is a complete disposable assembly, including a handle connected to the cable leading from the generator, the handle including an arrangement of socket or chuck for supporting various cutting components including interchangeable tips in the form of blades, needles or a ball for handling various surgical functions.

Referring to the drawings in which like reference characters refer to like parts throughout the several views thereof, FIG. 1 illustrates the invention as employed in a throw-away electrosurgical knife structure designated generally 10 having an elongated body 12 joining a connector portion 25 with an active tip 18. Active tip 18 includes a socket or chuck for receiving interchangeable cutting elements 20, which serve as the positive electrode for the electronic circuit forming the electrosurgical knife arrangement of the invention.

Positioned between the active tip 18 and the body 12 is the lens 16 for the warning light of the invention. As can be seen in FIG. 1, handle body 12 may have a plurality of elongated knurls circumferentially spaced around the outer surface thereof in order to enhance the gripping of body 12. Connector 25, as shown in FIG. 1 is connected to cable 14 leading from a plug 15 which is inserted into the generator for the circuit.

As stated above, while it is preferable to have disposable handles, particularly in this day and age of the fear of contamination from a patient's blood, such handles may be reusable, with interchangeable chucks or active tips which may be connected to the front end of the handle for, in turn, receiving, usually in a press-fit connection a plurality of interchangeable electrodes in the form of blades, needles or other tissue contacting arrangements. One of the difficulties with reusable devices of this kind is the requirement that they be sterilized. Sterilizing conditions have a tendency to weaken the electronic components of such an arrangement.

Moreover, the chuck may become loosened after repeated use. All of such difficulties make it appropriate and desirable to use throw-away arrangements in accordance with this invention.

Referring to FIG. 2(a), the figure shows the handle 12 in an exploded view to indicate more clearly the internal components as shown in FIG. 2(b). Referring to FIG. 2(b) a pin 24 is positioned in the connector portion 25, with pin 24 being arranged to be connected to one end of cable 14. The other end of pin 24, in turn, is connected to wire 26 which leads to the combination circuitry of the resistor 30 and lamp 28. Following the resistor 30, lamp 28, combination is a wire 38 connected to the opposite end thereof from wire 26 which wire 38 is in turn connected to blade receiver or chuck 32.

As can be seen in FIG. 2(b), the opposite end of blade receiver 32 includes a socket 34 for receiving a pluraliy of interchangeable cutting devices or blades such as 20 shown in FIG. 1.

Referring now to FIG. 3, a schematic illustration of the circuit diagram of the invention is shown. As can be seen in FIG. 3, generator 40 is connected with a connector 15 to cable 14 which, in turn, is connected to pin 24 at one end of handle 12. Pin 24, is in turn, connected to wire 26 which is connected at point 27 to the combination lamp 28, resistor 30. The opposite end of this combination designated generally 31 is connected at 33 to a wire 38 leading to the positive electrode in the form of a cutting instrument or blade 20.

The return structure for this circuitry of the invention includes a dispersive electrode 42 arranged to be positioned on the opposite side of a patient's body from the active electrode with the dispersive electrode 42 connected through a cable 44 to the generator 40. In this connection, it is conventional that the circuitry includes a foot pedal, not shown, for the surgeon to use to turn off the circuitry with the foot pedal being connected to the generator 40 by an additional cable for cutting off power to the active electrode 20.

As will be understood from the above discussion, the surgeon, in using the electrosurgical knife arrangement of the invention, in concentrating intently on the surgical site where he or she is applying the active electrode 32 has the lamp 28 in direct line of sight. Because of this, any fluctuation in the current in the circuit which might cause tissue damage, is immediately called to the surgeon's attention who in turn can immediately remove the active electrode from the surgical site prior to any deactivation by a pedal arrangement conventionally used to turn off the circuitry.

Thus, there is provided, in accordance with this invention, an electrosurgical active handle having a self-contained light source to designate specified current levels that are an indication of system faults, improper electrosurgical generator settings, or when operated in the visual region presenting an intensity of illumination related to a specific surgical procedure. During low current level surgical procedures, the visual portion of the active handle remains out or presents a dim glow on current peaks. However, on improper generator settings, or sudden system faults, the active handle produces a brilliant illumination warning the surgeon of possible tissue damage. Thus, in accordance with this invention, by selecting a lamp with a specified cold filament resistance and selecting a carbon resistor paralleled across the lamp, the invention achieves an arrangement wherein the active electrode may turn on at a specified current.

While the present invention comprehends the use of a low cost disposable active handle with interchangeable tips, it should be understood that it is within the purview of the invention, as discussed above, to use reusable handles. Such reusable operation requires certain limitations in the form of sterilization which causes rapid deterioration of the device after several uses and sterilization procedures. Moreover, the present invention comprehends an improved active handle construction wherein an electrical tungsten lamp is provided in the handle for effectively monitoring normal and dangerous currents if they occur during the surgical procedure.

While the forms of apparatus herein described constitute preferred embodiments of the invention, it is to be understood that the invention is not limited to these precise forms of apparatus, and that changes may be made therein without departing from the scope of the invention which is defined in the appended claims.

What is claimed is:

1. An electrosurgical handle apparatus, comprising
   (a) a handle body;
   (b) connector means at one end of said body for connection to a power source;
   (c) an active tip at the end of said handle body opposite said connector means for receiving a cutting instrument;
   (d) electronic flow communication means in said handle body, said electronic flow communication means extending through said handle body for carrying current between said active tip and said connector means;
   the improvement characterized by
   (e) a current responsive lamp in said electronic flow communication means;
   (f) a resistor in said electronic flow communication means; and
   (g) said lamp and said resistor being connected in parallel.

2. Apparatus according to claim 1, further characterized by
   (a) said active tip includes a chuck;
   (b) an electrosurgical blade frictionally received in said chuck; and
   (c) said blade forming the positive electrode of said handle.

3. Apparatus according to claim 1, further characterized by
   (a) a connecting pin in said connector means; and
   (b) an elongated cable connected at one end thereof to said pin.

4. Apparatus according to claim 1, further characterized by
   (a) said active tip includes a socket; and
   (b) a member selected from the group consisting of a needle, a blade or a ball received in said socket; and
   (c) said member forming the positive electrode of said handle.

5. A system for monitoring the electronic circuit connected to an electrosurgical device for unwanted variations in current during surgical procedures comprising;
   (a) a throw-away electrosurgical handle body;
   (b) a generator;
   (c) a connector pin at one end of said handle body;
   (d) an electric cable with one end connected to said generator and one end connected to said connector pin;

(e) an active electronic chuck at the end of said handle body opposite said connector pin;
(f) electronic flow communication means in said handle body, said electronic flow communication means extending through said handle body for carrying current between said electronic chuck and said connector pin;
(g) a dispersive electrode connected to said generator;

the improvement characterized by (h) a current responsive lamp in said electronic flow communication means;
(i) a resistor in said electronic flow communication means; and
(j) said lamp and said resistor being connected in parallel.

6. the system of claim 5, further characterized by
(a) a member selected from the group consisting of a blade, a pin or a ball received in said electronic chuck; and said member forming the positive electrode of said system.

* * * * *